United States Patent
Carls et al.

(10) Patent No.: US 9,011,539 B2
(45) Date of Patent: Apr. 21, 2015

(54) SPINAL NUCLEUS REPLACEMENT IMPLANT

(75) Inventors: Thomas Carls, Memphis, TN (US); Joshua Simpson, Collierville, TN (US); Jason John Eckhardt, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1507 days.

(21) Appl. No.: 12/356,743

(22) Filed: Jan. 21, 2009

(65) Prior Publication Data
US 2010/0185288 A1      Jul. 22, 2010

(51) Int. Cl.
*A61F 2/44*      (2006.01)
*A61F 2/30*      (2006.01)

(52) U.S. Cl.
CPC ............... *A61F 2/442* (2013.01); *A61F 2/441* (2013.01); *A61F 2002/30014* (2013.01); *A61F 2002/30242* (2013.01); *A61F 2002/30383* (2013.01); *A61F 2002/30471* (2013.01); *A61F 2002/305* (2013.01); *A61F 2002/30507* (2013.01); *A61F 2002/30579* (2013.01); *A61F 2002/30583* (2013.01); *A61F 2002/30584* (2013.01); *A61F 2002/30604* (2013.01); *A61F 2002/30754* (2013.01); *A61F 2002/444* (2013.01); *A61F 2210/0085* (2013.01);
(Continued)

(58) Field of Classification Search
CPC .......................................... A61F 2/44
USPC ...................................... 623/17.11
See application file for complete search history.

(56) References Cited

U.S. PATENT DOCUMENTS

| 4,777,947 A | 10/1988 | Zwick |
| 4,936,848 A | 6/1990 | Bagby |

(Continued)

FOREIGN PATENT DOCUMENTS

| CA | 2441384 A1 | 11/2002 |
| DE | 2804936 A1 | 2/1979 |

(Continued)

OTHER PUBLICATIONS

"Arthroplasty with Intercorporal Endoprothesis in Herniated Disc and in Painful Disc", from Dept. of Surgery, Uddevalla, Sweden, Suppl. 357, 1966.
(Continued)

*Primary Examiner* — Thomas J Sweet
*Assistant Examiner* — Matthew Schall (57) ABSTRACT

An intervertebral prosthesis implantable within a disc space and disposed between upper and lower vertebral endplates is provided. The prosthesis comprises a plurality of prosthesis modules insertable into the disc space, wherein the modules have at least one set of complementarily-shaped and sized surfaces, and wherein at least one of the modules is expandable. The modules have surfaces configured to engage within the disc space in a manner such that the modules form an assembled prosthesis of a size substantially preventing it from being outwardly expelled from the disc space, and the modules have bearing surfaces slidably engageable with the endplates to permit articulation between upper and lower vertebral endplates. In one embodiment, the at least one expandable module of the intervertebral prosthesis expands by inflation. In another embodiment, the at least one expandable module expands by unfolding into its intended form.

18 Claims, 5 Drawing Sheets

(52) U.S. Cl.
CPC  *A61F 2220/0025* (2013.01); *A61F 2220/0091* (2013.01); *A61F 2230/0071* (2013.01); *A61F 2250/0018* (2013.01); *A61F 2310/00017* (2013.01); *A61F 2310/00023* (2013.01); *A61F 2310/00029* (2013.01)

(56) References Cited

U.S. PATENT DOCUMENTS

| | | | |
|---|---|---|---|
| 5,059,193 | A | 10/1991 | Kuslich |
| 5,250,061 | A | 10/1993 | Michelson |
| 5,458,611 | A | 10/1995 | Resnick et al. |
| 5,472,010 | A | 12/1995 | Gonzalez |
| 5,645,596 | A | 7/1997 | Kim et al. |
| 5,743,918 | A | 4/1998 | Calandruccio et al. |
| 5,888,226 | A | 3/1999 | Rogozinski |
| 6,120,509 | A | 9/2000 | Wheeler |
| 6,436,101 | B1 | 8/2002 | Hamada |
| 6,478,822 | B1 | 11/2002 | Leroux et al. |
| 6,638,310 | B2 | 10/2003 | Lin et al. |
| 6,652,534 | B2 | 11/2003 | Zucherman et al. |
| 6,733,531 | B1 | 5/2004 | Trieu |
| 6,733,534 | B2 | 5/2004 | Sherman |
| 6,749,608 | B2 | 6/2004 | Garito et al. |
| 6,794,960 | B2 | 9/2004 | Chiu et al. |
| 7,001,433 | B2 | 2/2006 | Songer et al. |
| 7,267,692 | B2 | 9/2007 | Fortin |
| 2002/0120283 | A1 | 8/2002 | Holmes |
| 2002/0156528 | A1 | 10/2002 | Gau |
| 2003/0023308 | A1 | 1/2003 | Leroux et al. |
| 2003/0204261 | A1 | 10/2003 | Eisermann et al. |
| 2003/0220691 | A1 | 11/2003 | Songer et al. |
| 2004/0024461 | A1 | 2/2004 | Ferree |
| 2004/0030391 | A1 | 2/2004 | Ferree |
| 2004/0093082 | A1 | 5/2004 | Ferree |
| 2004/0102774 | A1* | 5/2004 | Trieu ........................ 606/61 |
| 2004/0176773 | A1 | 9/2004 | Zubok et al. |
| 2004/0186576 | A1 | 9/2004 | Biscup et al. |
| 2005/0015151 | A1 | 1/2005 | Fortin |
| 2005/0149188 | A1 | 7/2005 | Cook et al. |
| 2006/0095132 | A1 | 5/2006 | Kirschman |
| 2006/0106462 | A1 | 5/2006 | Tsou |
| 2006/0224240 | A1 | 10/2006 | Allard et al. |
| 2008/0086127 | A1 | 4/2008 | Patterson et al. |

FOREIGN PATENT DOCUMENTS

| | | |
|---|---|---|
| EP | 1354572 A2 | 10/2003 |
| WO | 9531948 | 11/1995 |
| WO | 02087480 A1 | 11/2002 |
| WO | 03099172 A1 | 12/2003 |
| WO | 2005081884 A2 | 9/2005 |
| WO | 2005086067 A1 | 9/2005 |

OTHER PUBLICATIONS

"Fernstrom Intervertebral Disc Arthroplasty: A Long-Term Evaluation", Alvin H. McKenzie, MD.

"Intervertebral Disc Prostheses", Guyer and Ohnmeiss, Spine vol. 28, No. 15S, Copyright 2003, Lippincott Williams & Wilkins, Inc., 9 pages.

"Intractable Headache and Cervico-Brachialgia Treated by Complete Replacement of Cervical Intervertebral Discs With a Metal Prosthesis", Reprinted from the "S.A. Medical Journal", vol. 38, Nov. 7, 1964, pp. 881-884.

"Satellite Interdiscal Stabilization Sphere Surgical Technique", 2004, Medtronic Sofamor Danek, USA, Inc., 5 pages.

* cited by examiner

SPINAL NUCLEUS REPLACEMENT IMPLANT

BACKGROUND

This disclosure is related to application Ser. Nos. 12/356,702 and 12/356,713, each of which is hereby incorporated by reference in their entireties.

The present disclosure relates generally to devices and methods for relieving disc degeneration or injury, and more particularly, to devices and methods for augmenting or replacing a nucleus pulposus. Within the spine, the intervertebral disc functions to stabilize and distribute forces between vertebral bodies. The intervertebral disc comprises a nucleus pulposus which is surrounded and confined by the annulus fibrosis (or annulus).

Intervertebral discs are prone to injury and degeneration. For example, herniated discs typically occur when normal wear, or exceptional strain, causes a disc to rupture. Degenerative disc disease typically results from the normal aging process, in which the tissue gradually loses its natural water and elasticity, causing the degenerated disc to shrink and possibly rupture.

Intervertebral disc injuries and degeneration may be treated by fusion of adjacent vertebral bodies or by replacing the intervertebral disc with a prosthetic. To maintain as much of the natural tissue as possible, the nucleus pulposus may be supplemented or replaced while maintaining all or a portion of the annulus.

It would be advantageous to keep any incision in the annulus minimal, in order to avoid injuring healthy tissue. Accordingly, it is desirable to provide a prosthetic device that requires a relatively small opening or incision in the annulus when being inserted into the disc space.

SUMMARY OF THE INVENTION

An intervertebral prosthesis implantable within a disc space and disposed between upper and lower vertebral endplates is provided. The prosthesis comprises a plurality of prosthesis modules insertable into the disc space, wherein the modules have at least one set of complementarily-shaped and sized surfaces, and wherein at least one of the modules is expandable. The modules have surfaces configured to engage within the disc space in a manner such that the modules form an assembled prosthesis of a size substantially preventing it from being outwardly expelled from the disc space, and the modules have bearing surfaces slidably engageable with the endplates to permit articulation between upper and lower vertebral endplates.

In one embodiment, the at least one expandable module of the intervertebral prosthesis expands by inflation. In another embodiment, the at least one expandable module expands by unfolding into its intended form.

Where inflation is used to expand the expandable module, the prosthesis further comprises at least one balloon situated within the at least one expandable module and inflation is accomplished by delivering an inflation material to the at least one balloon.

When unfolding is used to expand the expandable module, the expandable module comprises at least two components that are connected. In certain such embodiments, the expandable module comprises at least three subcomponents connected in series. In certain embodiments, the expandable module of the prosthesis of the present invention is inserted through the opening of the disc space when it is in a folded state.

In certain embodiments of the present invention, each module of the prosthesis is inserted into the disc space by being inserted through an opening in the annulus between the upper and lower vertebral endplates. In certain embodiments of the present invention, the modules are shaped and configured to form a generally spherical-shaped prosthesis.

According to certain aspects of the present invention, the expandable module has a plurality of components, wherein after being inserted into the disc space, the components expand to form the intended shape of the expandable module, and at least one module mates with the expandable module after it is expanded, to form the final shape of the prosthesis.

Additional aspects and features of the present disclosure will be apparent from the detailed description and claims as set forth below.

DETAILED DESCRIPTION

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
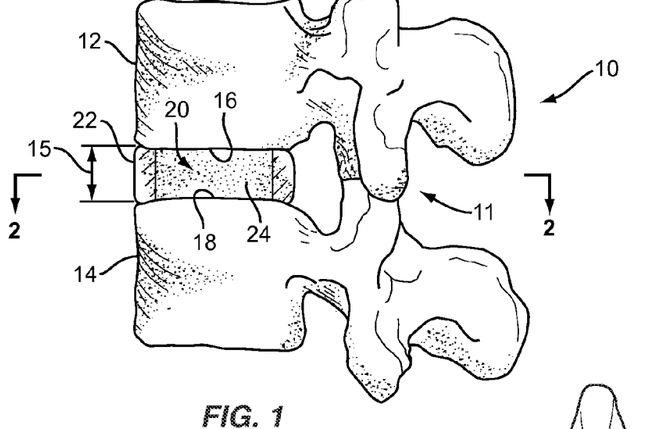
FIG. 1 is a cross-sectional lateral view of a section of a spinal column.

Referring first to FIG. 1, the reference numeral 10 refers to a vertebral joint section or a motion segment of a vertebral column. The joint section 10 includes adjacent vertebral bodies 12 and 14. The vertebral bodies 12 and 14 include endplates 16 and 18, respectively. An intervertebral disc space 20 is located between the endplates 16 and 18, and an annulus fibrosus 22 surrounds the space 20. In a healthy joint, the space 20 contains a nucleus pulposus 24 within the disc space 20, which helps maintain the distance between endplates 16 and 18, known as the disc height 15. Proper disc height 15 may vary for a particular patient, but medical experts understand how to determine a range of desired disc height 15. The nucleus pulposus 24 may degenerate with age, disease or trauma, permitting the endplates 16 and 18 to move closer together.

Figure 2:
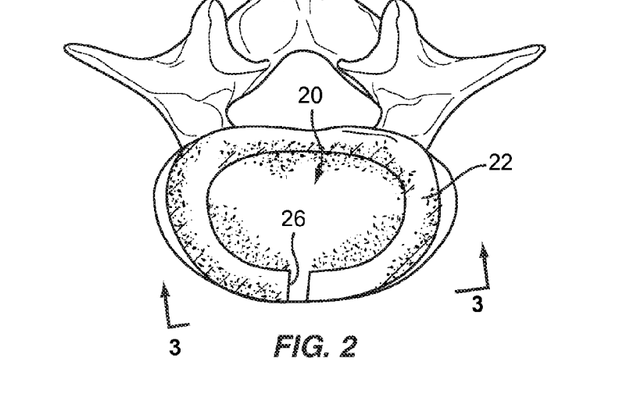
FIG. 2 is an exemplary disc incision in the anterior wall of an annulus fibrosus.
Figure 3:
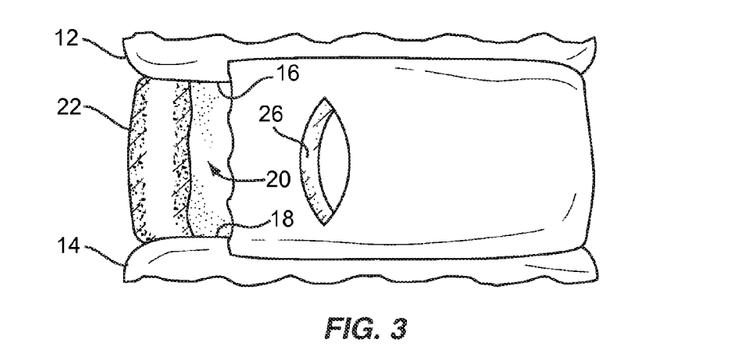
FIG. 3 is a cut-away, cross-sectional view of the layer of spinal column of FIG. 2.

Referring now to FIGS. 2 and 3, an exemplary disc incision 26 is shown in the anterior wall of the annulus fibrosus 22. Disc incision 26 breaches the annulus fibrosus 22 to the disc space 20. As necessary, nucleus pulposus 24 may be removed from the disc space 20 in order to accommodate the insertion of a prosthesis. Illustratively (representatively shown empty in FIG. 2), the disc incision 26 is longitudinal in order to attempt to minimize trauma to the annulus fibrosus 22. The anterior wall of the annulus fibrosus 22 is shown, but the depicted procedure and device are not limited by the example. The particular surgical professional performing the procedure may choose to enter the annulus fibrosus 22 from anterior oblique, posterior, posterior oblique, lateral, transforaminal, or any other approach judged suitable with regard to other factors. The particular surgical professional also may choose to orient the disc incision 26 differently.

A dilator may be used to dilate the disc incision 26, making it large enough to deliver the implant to replace or augment the disc nucleus. The dilator may stretch the disc incision 26 temporarily and avoid tearing so that the disc incision 26 can return back to its undilated size after the dilator instrument is removed. Although some tearing or permanent stretching may occur, the dilation may be accomplished in a manner that allows the disc incision 26 to return to a size smaller than the dilated size after the implantation is complete.

Figure 4A:
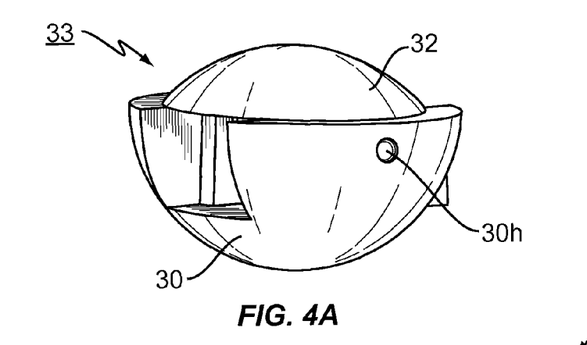
FIGS. 4A is an isometric view of a main module (or expandable module) of a prosthesis according to the present invention.
Figure 4B:
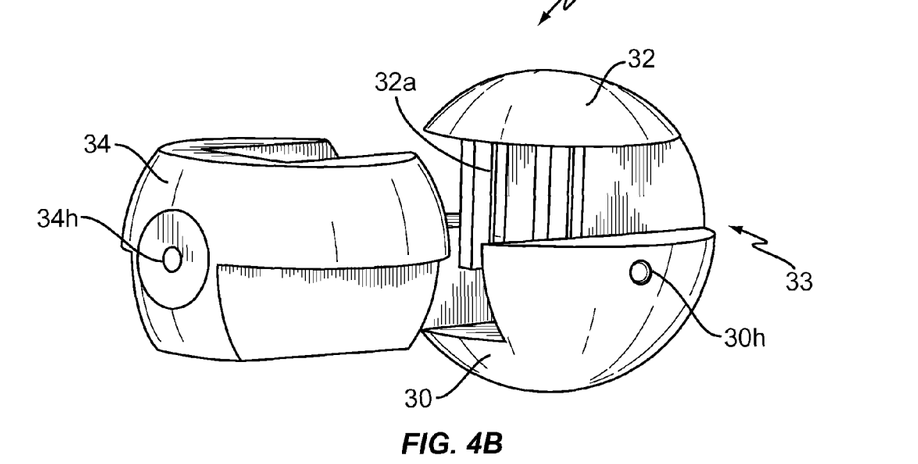
FIG. 4B is an isometric view of a second module along with main module of the prosthesis of FIG. 4A.
Figure 4C:
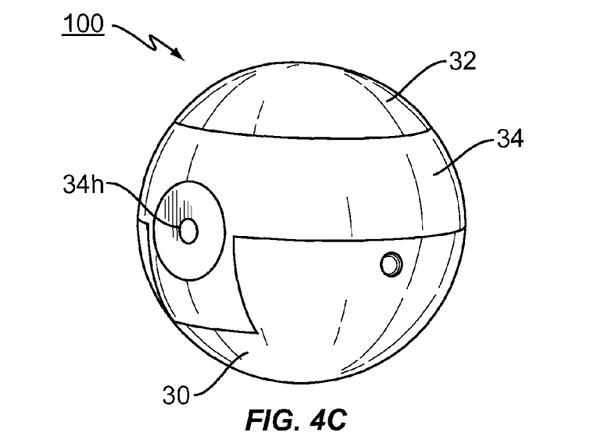
FIG. 4C is an isometric view of the prosthesis of FIG. 4A in its intended final shape.

FIGS. 4A, 4B and 4C show isometric views of a specially designed prosthesis 100 embodying principles of the present invention. FIG. 4A shows a main module 33 (or expandable module 33) comprising components 30 and 32 of the prosthesis 100. It is designed and intended for the main module 33 to have the shape as shown in FIG. 4A at the time of insertion through the annulus 22 and into the disc space 20. As explained, it is desired to have a relatively small profile (height and width) when a prosthesis is inserted into the disc space 20 through an incision 26 in the annulus 22. A prosthesis with a relatively small profile provides minimal disruption to the annulus 22. Also, it will provide minimal disruption to the apophyseal ring and associated posterior elements at the level between the vertebral bodies in question, such as vertebrae 12 and 14.

FIG. 4B shows an isometric view of module 34 along with main module 33 of the prosthesis 100 of the present invention. As shown in FIG. 4B, module 33 (comprising components 30 and 32) has taller profile than that of FIG. 4A. In FIG. 4A, components 30 and 32 have a nested configuration where component 32 is nesting within component 30. Module 33 achieves the configuration shown in FIG. 4B by means of inflation. For example, a balloon 29 (not shown in FIG. 4B) resides between the components 30 and 32 as shown in FIG. 4A. When such balloon is inflated, it causes components 30 and 32 to separate to achieve their intended ultimate shape, as shown in FIG. 4B.

Figures 5A, 5B:
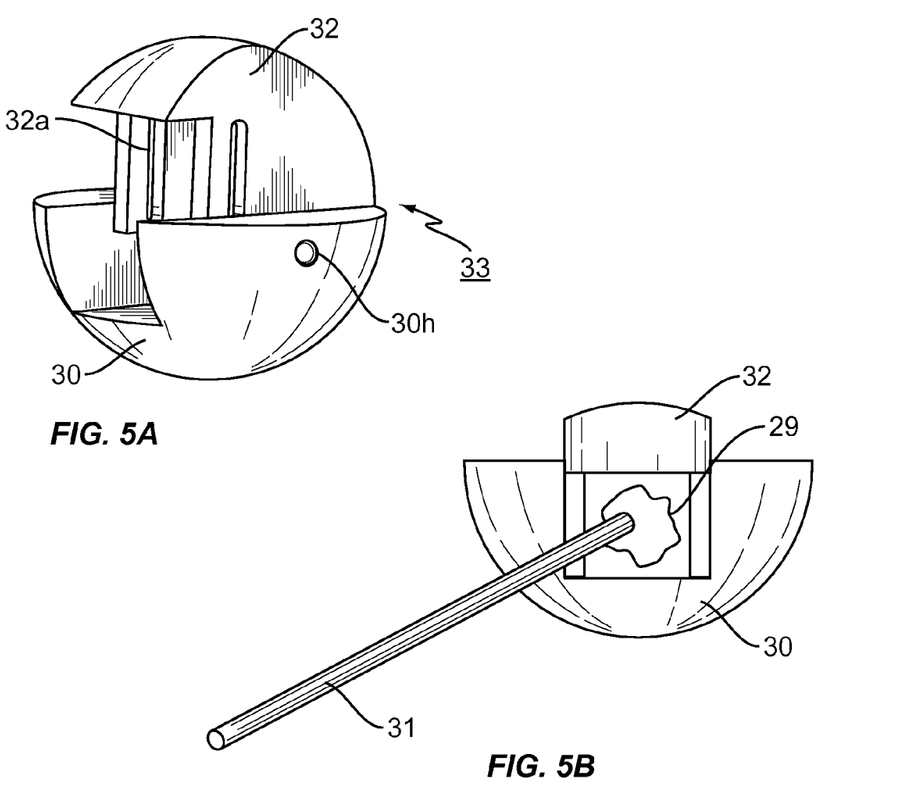
FIG. 5A is an isometric view of the expandable module of the prosthesis of FIGS. 4A-4C.
FIG. 5B is a side view of the expandable module of FIG. 5A prior to inflation.
Figure 5C:
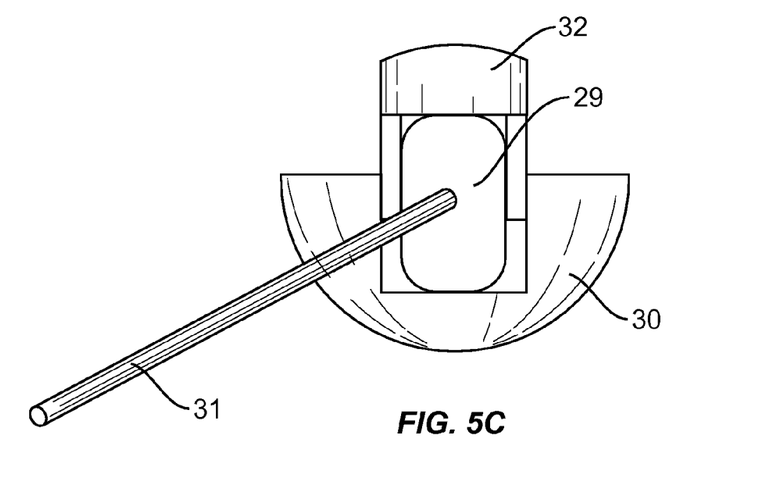
FIG. 5C is a side view of the expandable module 33 of FIG. 5A after inflation.

FIGS. 5A, 5B and 5C illustratively show the step of inflation of expandable module 33. FIG. 5A shows an isometric view of expandable module 33 in its inflated stage. Note that FIG. 5A is similar to FIG. 4B, but module 34 is missing from FIG. 5A. FIG. 5B shows a side view of module 33 prior to inflation, and depicts a viewpoint from another angle of the nested configuration of components 30 and 32. As shown in FIG. 5B, component 32 is shown un-inflated and a balloon 29 is shown along with a tube 31 (or other delivery device such as a syringe) used to deliver the fluid, gas, cement or other suitable material into the balloon 29 for inflation thereof. FIG. 5C shows a similar side view of expandable module 33 after inflation. That is, FIG. 5C depicts expandable module 33 after component 32 has been inflated with the inflation material by means of the delivery device 31. At this stage, expandable module 33 has taken on its inflated shape of module 33, as shown in FIGS. 5A or 4B. Note that balloon 29 already may reside in module 32 when it is inserted into the disc space 20, or balloon 29 may be inserted into module 32 some time thereafter, e.g., just before inflation begins. In addition, depending on the inflation material, the balloon 29 itself may be removed after inflation of the expandable module 33 occurs. Note also that, as shown in FIGS. 4B and 4C, module 34 has a hole 34h to accommodate the delivery device 31 if, for example, inflation occurs after module 34 is in place, or access to the balloon 29 is necessary after module 34 is in place.

After the step of inflation is accomplished, module 34 may then be inserted through the incision 26 in the annulus 22 into the disc space. FIG. 4B shows the two modules of the prosthesis 100 prior to the insertion and implantation of module 34. FIG. 4C shows an isometric view of the prosthesis 100 in its intended shape, which is generally-spherical. In its final shape, each of the modules 33 (which includes components 30 and 32) and 34 have complementarily-shaped and sized surfaces so that they mesh or nest with each other so that the final prosthesis is stable and has an overall generally-spherical shape. Note that with the embodiment of the prosthesis 100 as shown in FIGS. 4A-4C, the module 34 locks in place with module 33 with a connection mechanism. As shown in FIG. 4B, part of this connection mechanism is shown as locking segments 32a on component 32. In turn, module 34 has a shape or specific locking segments (not shown) that mate with the segments 32a. Such locking mechanisms can be quick connects, snap fits, living hinges or other mechanisms. Alternatively, a locking mechanism different than that shown can be employed, such as a set screw. Similarly, note that module 30 has a hole 30h to accommodate a pin (not shown) that helps component 32 move by way of slots of locking segments 32a.

Note that the final shape of prosthesis 100 need not be perfectly spherical, or even generally-spherical. Further, the modules 33 and 34 have surfaces configured to engage within the disc space in a manner that the modules 33 and 34 form an assembled prosthesis 100 of a size substantially preventing it from being outwardly expelled from the disc space through the opening. In addition, the modules 30 and 33 have bearing surfaces slidably engageable with the endplates 16 and 18 of the adjacent vertebral bodies 12 and 14 to permit articulation between vertebral endplates 16 and 18. Lastly, while the final shape of prosthesis 100 is generally-spherical, when they are inserted through incision 26 of the annulus 22, each of the modules 30 and 33 have a smaller height profile than the final shape.

Figure 6A:
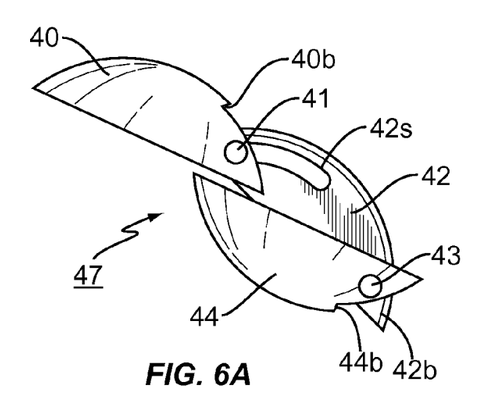
FIG. 6A is a side view of a main module of a prosthesis according to the present invention in its folded configuration.

FIGS. 6A, 6B, 6C and 6D show various views of a specially designed prosthesis 200 according to the present invention. FIG. 6A shows a side view of a main module 47, which comprises components 40, 42 and 44, of the prosthesis 200. It is designed and intended for the prosthesis 100 to have the shape as shown in FIG. 6A, also called a folded configuration or folded state of module 47, at the time of insertion through the annulus 22 and into the disc space 20. As explained above, it is desired to have a relatively small profile (height and width) when a prosthesis is inserted into the disc space 20 through an incision 26 in the annulus 22. Specifically, FIG. 6A shows three components 40, 42 and 44 of module 47 connected in series. Component 40 is connected to component 42 by means of rod 41 so that the two are connected but still able to rotate with respect to each other. Similarly, component 44 is connected to component 42 by means of a rod 43.

Figure 6B:
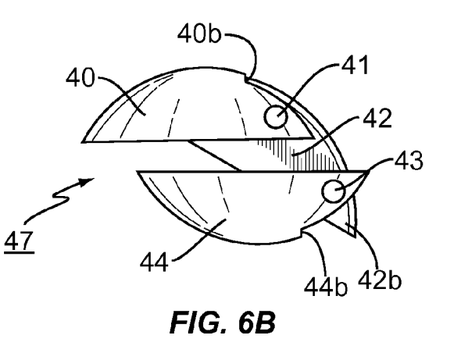
FIG. 6B is a side view of components of the main module of FIG. 6A as each are rotating towards their intended position and shape.
Figure 6C:
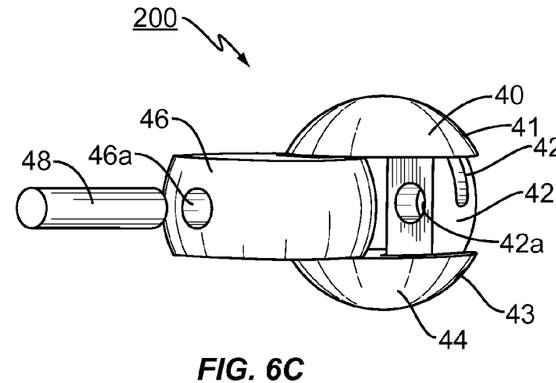
FIG. 6C is an isometric view of all of the parts of the prosthesis of FIG. 6A prior to final assembly.

FIG. 6B shows a side view of components 40, 42 and 44 as each are rotating towards their intended position and shape, or unfolding of module 47, which begins after components 40, 42 and 44 of module 47 are inside the disc space 20. FIG. 6C shows an isometric view of the prosthesis 200, where components 40, 42 and 44 of module 47 are in their intended and unfolded configuration. Further, to help module 47 maintain its final shape, components 40 and 44 may have ridges 40b and 44b, respectively. In this way, for example, the end 42b of component 42 may fit snugly or even snap into place with ridge 44b of component 44. Similarly, the other end of component 42 may mate with respective ridge 40b of component 40.

Once module 47 is unfolded in its final configuration, module 46 can be inserted into the disc space through the incision 26. After module 46 is in place, connecting element 48 can be inserted through the incision 26 and into place. As shown in FIG. 6C, connecting element 48 can then be inserted through hole 46a of module 46 and into hole 42a of component 42 of module 47. In doing so, connecting element 48 connects the modules 47 and 46 together. With prosthesis 200, connecting element 47 is a locking mechanism that can be a set screw, a snap fit or other locking mechanism.

As with prosthesis 100, the intended final shape of prosthesis 200 also is generally-spherical. Similarly, in its final shape, each of the modules 47 (which includes components 40, 42 and 44) and 46 have complementarily-shaped and sized surfaces so that they mesh or nest with each other so that the final prosthesis is stable and has an overall generally-spherical shape. Note, however, that the final shape of prosthesis 200 (as with prosthesis 100) need not be perfectly spherical, or even generally-spherical. Further, as with prosthesis 100, the modules 47 and 46 have surfaces configured to engage within the disc space in a manner that the modules 47 and 46 form an assembled prosthesis 200 of a size substantially preventing it from being outwardly expelled from the disc space through the opening. In addition, the modules 47 and 46 have bearing surfaces slidably engageable with the endplates 16 and 18 of the adjacent vertebral bodies 12 and 14 to permit articulation between vertebral endplates 16 and 18. Lastly, while the final shape of prosthesis 100 is generally-spherical, when they are inserted through incision 26 of the annulus 22, each of the modules 47 and 46 have a smaller height profile than the final shape.

Figure 6D:
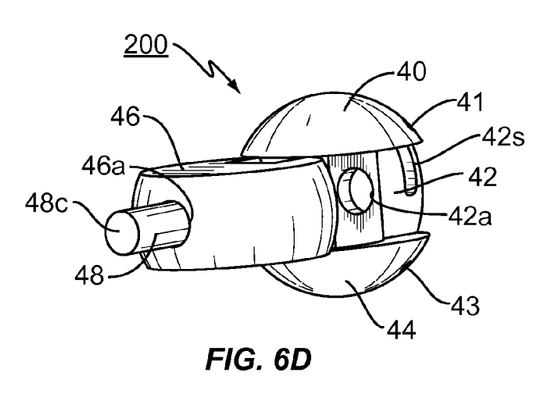
FIG. 6D is another isometric view of all of the parts of the prosthesis of FIG. 6A prior, but closer to, final assembly that the state shown in FIG. 6C.

FIG. 6D shows an isometric view of an embodiment of prosthesis 200 of the present invention. Specifically, FIG. 6D shows a prosthesis 200 after connecting element 48 already has been partially inserted into hole 46a of module 46. Further, FIG. 6D also shows an optional slot 42s on component 42. This slot 42s can allow for component 40 to slide back closer to component 44 to change the shape or at least, reduce the length of module 47 prior to its insertion through the incision 26 of the annulus 22.

Figure 7A:
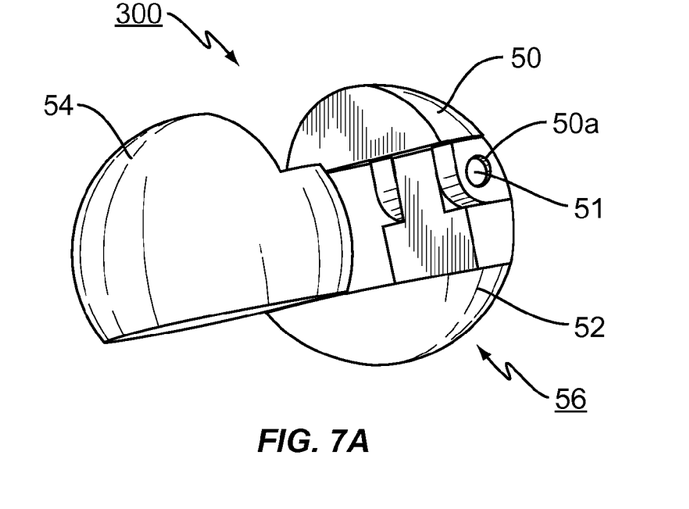
FIG. 7A is an isometric view of all of the parts of a prosthesis according to the present invention just prior to final assembly.
Figure 7B:
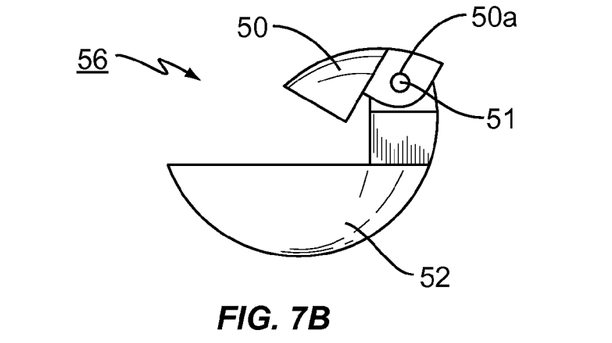
FIG. 7B is a side view of a main module of the prosthesis of FIG. 7A.
Figure 7C:
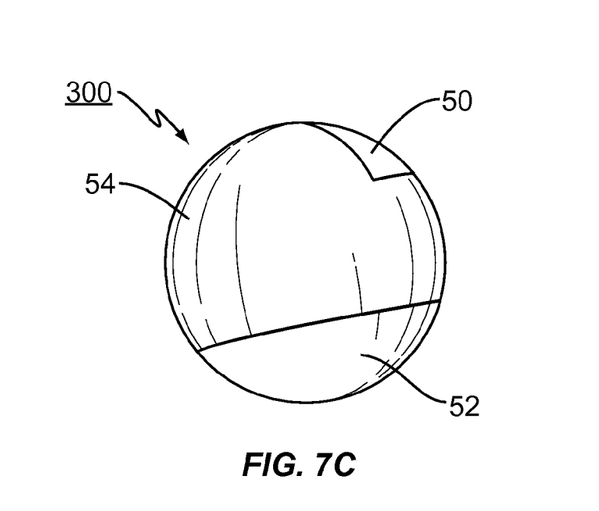
FIG. 7C is a side view of the prosthesis of FIG. 7A in its final shape.

FIGS. 7A, 7B and 7C show various views of a specially designed prosthesis 300 according to the present invention. FIG. 7A shows an isometric view of a module 54, and a main module 56, which comprises components 50 and 52 of the prosthesis 300. FIG. 7B shows a side view of main module 56. FIG. 7C shows the prosthesis 300 in its final shape. It is designed and intended for the prosthesis main module 56 to have the shape as shown in FIG. 7B, also called a folded configuration or folded state of module 56, at the time of insertion through the annulus 22 and into the disc space 20. As explained above, it is desired to have a relatively small profile (height and width) when a prosthesis is inserted into the disc space 20 through an incision 26 in the annulus 22. Specifically, FIG. 7B shows components 50 and 52 of module 56 connected, but component 50 is folded, or rotated downward toward component 52. Component 50 is connected to component 52 by means of rod 51 so that the two are connected but still able to rotate with respect to each other.

FIG. 7A shows a view of components 50 and 52 after module 51 is inserted into the disc space 20, and after each of components 50 and 52 have been unfolded (or rotated) to their intended position and shape. After that is accomplished, module 54 can be inserted through the incision 26 of annulus 22 into the disc space 20 and mated with module 56. After module 56 is in place, a connecting element (not shown) similar to element 48 can be inserted through the incision 26 and into place to connect modules 54 and 56. As shown in FIG. 7A, however, module 54 is connected to module 56 by means of a locking mechanism, such as a quick connect, snap fit, living hinge or other mechanism. Alternatively, a locking mechanism different than that shown can be employed, such as a set screw.

As with prostheses 100 and 200, the intended final shape of prosthesis 300 also is generally-spherical (with module 54 placed in all the way to mate with module 56). FIG. 7C shows a side view of the prosthesis 300 in its intended final shape, which is generally-spherical. As shown, module 54 is placed in position with module 56. When prosthesis 300 is in its final shape, each of the modules 56 (which includes components 50 and 52) and 54 have complementarily-shaped and sized surfaces so that they mesh or nest with each other so that the final prosthesis is stable and has an overall generally-spherical shape. Note, however, that the final shape of prosthesis 300 (as with prostheses 100 and 200) need not be perfectly spherical, or even generally-spherical. Further, as with prostheses 100 and 200, the modules 56 and 54 have surfaces configured to engage within the disc space in a manner that the modules 56 and 54 form an assembled prosthesis 300 of a size substantially preventing it from being outwardly expelled from the disc space through the opening. In addition, the modules 56 and 54 have bearing surfaces slidably engageable with the endplates 16 and 18 of the adjacent vertebral bodies 12 and 14 to permit articulation between vertebral endplates 16 and 18. Lastly, while the final shape of prosthesis 300 is generally-spherical, when they are inserted through incision 26 of the annulus 22, each of the modules 56 and 54 have a smaller height profile than the final shape.

As demonstrated above, prostheses 100, 200 and 300 of the present invention all require a relatively small opening (or incision 26) in the annulus 22 so that each prosthesis may be inserted into the disc space 20 by using multiple parts or modules, so that that each have a smaller profile than the final design. By using a design requiring inflation or a folding design, once inserted into the disc space, these multiple parts can expand, and after mating with other parts, form the final intended shape.

In each of the above prosthesis, the final intended shape is generally-spherical. A generally-spherical shape operates well within the disc space 20 in that it fits the natural curvature of the vertebral endplate geometry for adequate fixation, retention of motion, and stress distribution. The size of the generally-spherical shape is particularly important in the caudal-rostral dimension for disc height and re-stabilization of the disc space 20.

The present invention does not depend on the materials of the constituent parts, but any of components or modules may be made of any biocompatible materials that are typically used in the intra-discal area. Examples of suitable materials include, but are not limited to, metals such as cobalt-chromium alloys, stainless steels, titanium and titanium alloys. Examples of other materials include, but are not limited to, polymers such as polyetherether ketone ("PEEK"), polyether ketone ("PEK"), polyethylene, and polyurethanes. In addition, various ceramics, biologics and resorbable materials also could be used. Also, a portion of or whole component or module that is on the interior of any of the prostheses of the present invention can be made of a different material than the remainder of the component or module such that the prosthesis can have variable stiffness. Similarly, certain components or modules that occupy the central area of a prosthesis (e.g., module 46 of prosthesis 200) can be made of a compressible material to provide different load bearing characteristics.

Although only a few exemplary embodiments have been described in detail above, those skilled in the art will readily appreciate that many modifications are possible in the exemplary embodiments without materially departing from the novel teachings and advantages of this disclosure. An example of such a modification would be adapting an egg-like shaped outer body to receive a generally spherical inner body. An additional example would be to alter the orientation of the guide passage such that it does not pass through the center of a prosthesis component.

Accordingly, all such adjustments and alternatives are intended to be included within the scope of the invention, as defined exclusively in the following claims. Those skilled in the art should also realize that such modifications and equivalent constructions or methods do not depart from the spirit and scope of the present disclosure, and that they may make various changes, substitutions, and alternations herein without departing from the spirit and scope of the present disclosure. Furthermore, as used herein, the terms components and modules may be interchanged. It is understood that all spatial references, such as "anterior," "posterior," "inward," "outward," and "sides" are for illustrative purposes only and can be varied within the scope of the disclosure.

The invention claimed is:

1. An intervertebral prosthesis implantable within a disc space and disposed between upper and lower vertebral endplates, the prosthesis comprising a plurality of prosthesis modules insertable into the disc space wherein at least one of the modules is expandable and at least one of the modules is fixed, the expandable module comprising a first cavity comprising planar upper and lower surfaces and a second cavity extending transverse to the first cavity comprising a planar bottom surface between planar side surfaces, the fixed module comprising an upper portion including a planar upper surface engaged with the upper surface of the first cavity and a planar intermediate surface engaged with the lower surface of the first cavity, the fixed module further comprising a lower portion including a planar bottom surface engaged with the bottom surface of the second cavity extending between planar side surfaces engaged with the side surfaces of the second cavity such that the modules form a spherical-shaped assembled prosthesis of a size substantially preventing it from being outwardly expelled from the disc space through an opening in the disc space, the modules having bearing surfaces that are slidably engageable with the endplates to permit articulation between upper and lower vertebral endplates.

2. The intervertebral prosthesis of claim 1, wherein the at least one expandable module expands by inflation.

3. The intervertebral prosthesis of claim 1, wherein the at least one expandable module expands by unfolding into its intended form.

4. The intervertebral prosthesis of claim 2, wherein at least one balloon is situated within the at least one expandable module and inflation is accomplished by delivering an inflation material to the at least one balloon.

5. The intervertebral prosthesis of claim 3, wherein the expandable module comprises at least two components that are connected.

6. The intervertebral prosthesis of claim 5, wherein the expandable module is inserted through the opening in the disc space when it is in a folded state.

7. The intervertebral prosthesis of claim 6, wherein each module of the prosthesis is inserted into the disc space by being inserted through an opening in the annulus between the upper and lower vertebral endplates.

8. The intervertebral prosthesis of claim 3, wherein the modules are shaped and configured to form a generally spherically-shaped prosthesis.

9. The intervertebral prosthesis of claim 1, wherein:
the expandable module has a plurality of components, wherein after being inserted into the disc space, the components expand to form the intended shape of the expandable module; and
the fixed module mates with the expandable module after it is expanded, to form the final shape of the prosthesis.

10. The intervertebral prosthesis of claim 9, wherein when the prosthesis is in its final shape, the plurality of modules are locked together with a locking mechanism.

11. The intervertebral prosthesis of claim 2, wherein when the prosthesis is in its final shape, the plurality of modules are locked together with a locking mechanism.

12. The intervertebral prosthesis of claim 3, wherein when the prosthesis is in its final shape, the plurality of modules are locked together with a locking mechanism.

13. The intervertebral prosthesis of claim 9, wherein the expandable module includes three subcomponents connected in series.

14. The intervertebral prosthesis of claim 10, wherein the expandable module includes three subcomponents connected in series.

15. An intervertebral prosthesis implantable within a disc space, disposed between upper and lower vertebral endplates, the prosthesis comprising a plurality of prosthesis modules insertable into the disc space, wherein at least one of the modules is expandable by inflation and at least one of the modules is fixed, the expandable module comprising a first cavity comprising planar upper and lower surfaces and a second cavity extending transverse to the first cavity comprising a planar bottom surface between planar side surfaces, the fixed module comprising an upper portion including a planar upper surface engaged with the upper surface of the first cavity and a planar intermediate surface engaged with the lower surface of the first cavity, the fixed module further comprising a lower portion including a planar bottom surface engaged with the bottom surface of the second cavity extending between planar side surfaces engaged with the side surfaces of the second cavity such that the modules form a spherical-shaped assembled prosthesis of a size substantially preventing it from being outwardly expelled from the disc space through an opening in the disc space the modules having bearing surfaces slidably engageable with the endplates to permit articulation between upper and lower vertebral endplates.

16. The intervertebral prosthesis of claim 10, wherein the locking mechanism comprises locking segments on each of the plurality of modules configured to mate with one another to lock the plurality of modules together.

17. The intervertebral prosthesis of claim 16, wherein the locking segments are selected from the group consisting of quick connects, snap fits and living hinges.

18. The intervertebral prosthesis of claim 1, wherein the expandable module is movable between a first configuration in which the upper and lower surfaces of the first cavity engage one another and a second configuration in which the upper and lower surfaces of the first cavity are spaced apart from one another.

\* \* \* \* \*